United States Patent [19]
Childers

[11] Patent Number: 5,286,448
[45] Date of Patent: Feb. 15, 1994

[54] METHOD OF DECONTAMINATING A CHAMBER THAT HAS MOVABLE SHELVES

[75] Inventor: Robert W. Childers, Garner, N.C.

[73] Assignee: American Sterilizer Company, Erie, Pa.

[21] Appl. No.: 13,429

[22] Filed: Feb. 4, 1993

[51] Int. Cl.$^5$ .......................... A61L 2/00; A61L 9/00
[52] U.S. Cl. ...................................... 422/28; 422/33; 422/292; 422/295; 422/297; 422/302
[58] Field of Search ................... 422/28, 33, 292, 295, 422/297, 302; 108/92, 93, 96

[56] References Cited

U.S. PATENT DOCUMENTS

| | | | |
|---|---|---|---|
| 4,169,123 | 9/1979 | Moore et al. | 422/29 |
| 4,195,061 | 3/1980 | Kalasek | 422/109 |
| 4,230,663 | 10/1980 | Forstrom et al. | 422/33 |
| 4,406,861 | 9/1983 | Beauvais et al. | 422/113 |
| 4,512,951 | 4/1985 | Koubek | 422/33 |
| 4,642,165 | 2/1987 | Bier | 203/12 |
| 4,744,951 | 5/1988 | Cummings et al. | 422/28 |
| 4,863,688 | 9/1989 | Schmidt et al. | 422/28 |
| 4,909,999 | 3/1990 | Cummings et al. | 422/298 |
| 4,941,519 | 7/1990 | Sestak et al. | 141/22 |
| 4,948,566 | 8/1990 | Gabele et al. | 422/107 |
| 4,952,370 | 8/1990 | Cummings, et al. | 422/28 |
| 4,956,145 | 9/1990 | Cummings et al. | 422/28 |
| 5,008,079 | 4/1991 | Wutzler et al. | 422/28 |
| 5,019,345 | 5/1991 | Lorenz | 422/26 |
| 5,044,141 | 9/1991 | Franchi | 53/431 |
| 5,068,087 | 11/1991 | Childers | 422/26 |

OTHER PUBLICATIONS

R. F. Ryan "Operational Control and Optimization of Lyophilization Cycles and Equipment", Jun. 1992.
Brian Vaz, "Dynamic Vapor Penetration of Sterilizing Mixtures," 1985.
Johnson, "Vaporized Hydorgen Peroxide Sterilizing of Freeze Dryers," Nov. 1992.
"Lypohilizer Operational Qualification," date prior to 1992, Leyhold-Heraeus, date prior to 1992.
Graham, "Sterilization of Isolators and Lyophilizers with Hydrogen Peroxide in the Vapor Phase", Feb. 1992.
Vesley, et al., "Decontamination, Sterilization, Disinfection, and Antisepsis in the Microbiology Laboratory", 1986.

Primary Examiner—Robert J. Warden
Assistant Examiner—Krisanne M. Thornton
Attorney, Agent, or Firm—Jones, Day, Reavis & Pogue

[57] ABSTRACT

A method of decontaminating or sterilizing chamber systems including freeze dryers at low temperature and pressure levels by utilizing vaporized sterilant, preferably hydrogen peroxide, peracetic acid and mixtures thereof is disclosed.

22 Claims, 2 Drawing Sheets

METHOD OF DECONTAMINATING A CHAMBER THAT HAS MOVABLE SHELVES

FIELD OF THE INVENTION

The present invention relates to a method for decontaminating an evacuated chamber having movable shelves containing or comprised of complex and irregularly shaped articles. More particularly, the invention relates to a method of introducing a sterilant vapor into an evacuated chamber by utilizing the movable shelves within the chamber to controllably release the vapor. The sterilant vapor is left in the chamber for a sufficient period of time to produce the desired level of decontamination.

BACKGROUND OF THE INVENTION

Chambers are used in many industries including the food and drug industries for many different purposes; freeze drying and sterilization are two such purposes. Freeze dryers used in the pharmaceutical and other industries traditionally include a freeze dryer chamber, shelves in the chamber for holding the product(s) to be freeze dried, a condenser with refrigerator coils, a vacuum system, and piping for connecting the freeze dryer components. Generally, the freeze dryer shelves are heated and cooled during the freeze drying cycle with heating and cooling means, such as a heat transfer fluid circulating through the shelves and a heat exchanger.

Typically, the products to be freeze dried are in loosely capped containers, which are then placed on the freeze dryer shelves. After the chamber door is closed, the shelves are cooled to about −40° C. to freeze the product. Thermocouples, or other temperature probes, indicate when the product is frozen and at the correct temperature. The freeze dryer chamber and condenser are then evacuated through a top, side or rear port on the condenser to a deep vacuum of about 200 microns of Hg (1 Torr=1000 micron of Hg=1 mm of Hg) while the condenser coils are cooled to around −40° C. As sublimation of moisture from the product occurs, it cools the product further. The shelves are warmed to maintain the frozen product at the desired temperature.

The vaporous moisture from the product escapes from the loosely capped containers and is drawn in vapor form from the containers in the chamber to the condenser. In the condenser, the vapor condenses and then freezes on the condenser coils.

This process continues until the product is sufficiently freeze dried as determined by known means. The chamber is vented to atmospheric pressure, the containers are capped (if it is desired), the chamber door is opened, and the freeze dried product removed.

Traditionally, the condenser is defrosted before the next freeze drying cycle using water or steam. The water or steam may be flowed through the condenser or it may be used to flood the condenser. The chamber is typically isolated from the condenser during this process by a large butterfly or mushroom valve. The condenser is drained at the end of the defrost. The chamber is typically Cleaned-In-Place (C.I.P.) either manually or automatically between each load to remove any debris from the previous load.

Decontamination and sterilization of the chambers is currently accomplished using formaldehyde vapor, ethylene oxide gas, peracetic acid, liquid hydrogen peroxide, or steam. Each of these methods presents serious disadvantages. For the purposes of this invention the term decontamination means a 3 log (or greater) reduction in bioburden and sterilization means a 6 log (or greater) reduction in bioburden.

Methods using formaldehyde vapor and ethylene oxide gas typically operate at pressures below 15 psig and at temperatures below 140° F.; however, the sterilizing agents are undesirable because they are considered carcinogenic and may be harmful to the operator. Residual removal is also a problem. Ammonia is used to neutralize the formaldehyde gas, leaving a white powder distributed throughout the freeze dryer which is difficult to remove without compromising sterility.

Ethylene oxide vapors can be removed and catalyzed during a lengthy aeration (i.e. more than 8 hours); however, various air/ethylene oxide mixtures which are present during the decontamination/sterilization process are explosive. Consequently, ethylene oxide is typically mixed with Freon 12, an ozone depletor which must be recovered at great expense.

Peracetic acid and liquid hydrogen peroxide may also be sprayed manually, or automatically, throughout the interior of freeze dryers. This method, though, is ineffective on inaccessible areas such as the condenser and "dead legs" (dead-ended piping or lumens) in the freeze dryer unit. Completely flooding the freeze dryer is also not effective since air pockets will prevent the liquid from penetrating into many of the same inaccessible areas.

Steam is emerging as the method of choice. Steam sterilization, however, is achieved at very high temperatures and pressures. As a result, this method requires that the freeze dryer chamber, condenser and associated piping be subjected to high temperature and pressure. The combined high pressure and temperature of steam sterilization (e.g., 250° F. and 15 psig) when alternated with freeze drying while deeply evacuated (at −40° F. and at approximately 200 microns of Hg absolute) takes its toll on the reliability of the freeze dryer system. Furthermore, existing freeze dryers which do not meet the required temperature/pressure requirements cannot be retrofit for steam decontamination/sterilization.

There is a need for a method which can decontaminate or sterilize chambers, particularly freeze dryers, in an economical and simple manner. There is a further need for a method for decontaminating or sterilizing chambers, particularly freeze dryers, that can be applied on existing chambers and freeze dryers. There is also a need for a method for decontaminating or sterilizing chambers particularly freeze dryers, without using hazardous sterilants or chemicals having hazardous decomposition products which are harmful to the environment.

SUMMARY OF INVENTION

It is therefore a main object of the present invention to provide a method of effectively decontaminating, and preferably sterilizing, chambers, particularly freeze dryers, in a simple and economical manner, without using hazardous sterilants or chemicals having hazardous decomposition products.

Additional objects and advantages of the invention will be set forth in part in the description which follows, and in part will be obvious from the description, or may be learned by practice of the invention. The objects and advantages of the invention may be realized and obtained by means of instrumentalities and combinations particularly pointed out in the appended claims.

To achieve these objects and in accordance with the purpose of the invention, the present invention provides a method of decontaminating, preferably sterilizing, a chamber system, particularly freeze dryer system, with sterilant vapor, preferably hydrogen peroxide or peracetic acid vapor, at the completion of the freeze drying cycle, wherein the freeze dryer comprises a freeze dryer chamber containing at least two shelves, one of which is movable, and a condenser, which are fluidly coupled to each other. Actual decontamination/sterilization is accomplished by placing a container or containers holding a predetermined amount of liquid sterilant between the shelves in the freeze dryer chamber, lowering the shelves thereby sealing the container(s), deeply evacuating the freeze dryer components, raising the shelves which allows the liquid sterilant to vaporize by exposing it to the evacuated environment, and exposing the freeze dryer components to the vapor for a predetermined period. This process is then repeated until a predetermined level of decontamination is achieved. An aeration follows. consisting of alternating system evacuation and venting until all residuals have been removed.

The method may also be applied on a freeze dryer chamber least two shelves are vertically movable while maintaining position horizontally.

The method may also be combined with a container apparatus comprising multiple individual containers, wherein each container comprises a compression spring, plunger, sealing device and a stop which varies in length for each container, thereby allowing multiple sterilization pulses to occur on any one movable shelf.

DETAILED DESCRIPTION OF THE PREFERRED EMBODIMENT

The present invention overcomes the disadvantages of current sterilization methods by first placing a predetermined amount of liquid sterilant, preferably liquid hydrogen peroxide or peracetic acid, in one or more containers. The containers are uniformly distributed on a lower shelf of the chamber having at least two shelves, wherein an upper shelf may be moved vertically without altering its position horizontally. The uniform distribution of containers prevents the shelf raise/lower mechanism from binding and/or being damaged and may improve vaporization efficiency. Each container comprises a compression spring and sealing device which may be broken in order to expose the contents to the chamber environment. In determining the amount of sterilant liquid which should be placed inside the container, the combined chamber and condenser volume and sterilant concentration are considered For example, a freeze dryer with a combined chamber and condenser volume of 100 liters (3.53 ft.$^3$) would accept 2.2 mg/liter of 35% by weight of $H_2O_2$ vapor at 25° C. without exceeding below the dew point of the vapor. Accordingly, the following calculation is performed.

2.2 mg/liter × 100 liters × 0.001 gram/mg × 100 g solution/35 g $H_2O_2$ = 0.628 g solution.

The dew point can be calculated for a given chamber temperature and hydrogen peroxide solution concentration by using methodology outlined in U.S. Pat. No. 4,956,145, the disclosure from which is incorporated by reference herewith.

For functional, as well as safety reasons, not more than 1 or 2 grams of solution should be placed in one container. The mass of liquid hydrogen peroxide must be small compared to the mass of the container so that the evaporative cooling of the sterilant is offset by heat transfer from the container thereby preventing freezing. The liquid, however, can be divided among several containers that are, for example, located in the center and each of the four corners of the shelf.

A loosely fitted cap is placed on the liquid filled container. The upper chamber shelf is lowered in order to press down on the container cap and, hence, seal the containers. The chamber, condenser and piping are then evacuated and the vacuum valves closed isolating the freeze dryer system from the vacuum system. Following evacuation the upper shelf is raised until the seals on the containers have been broken, allowing the exposed hydrogen peroxide to evaporate in the deeply evacuated environment. The system remains under a deep vacuum for a pre-determined time period, exposing the interior of the freeze dryer to the hydrogen peroxide vapor. The pressure rise corresponding to the vaporization of the solution is dependent on both temperature and concentration of the solution. Sterilization of all or the interior of the freeze dryer, condenser and piping will likely be incomplete in dead legs when most of the hydrogen peroxide vapor from a single exposure has broken down into water vapor and oxygen. Hence, the above mentioned steps are then repeated until a predetermined level of decontamination or sterilization is achieved. After decontamination/sterilization has been achieved, the system is aerated by alternating system evacuation and venting until all residuals have been removed.

In a first embodiment of the invention, the freeze dryer chamber includes two shelves, upper and lower, the upper one of which is movable. A container holding a predetermined amount of liquid sterilant, preferably hydrogen peroxide or peracetic acid, more preferably about 30–35% by weight concentration of aqueous solution of hydrogen peroxide, is loosely capped and placed within the freeze dryer chamber at the center of the lower shelf. Four additional empty containers are placed in each of the four corners of the chamber, preventing the shelf raise/lower mechanism from binding and/or being damaged. Alternately, the liquid sterilant may be distributed among the containers thereby improving vaporization efficiency. The upper shelf is then lowered until it presses on the cap and seals the liquid filled container. The chamber, condenser and piping are evacuated to below 1 Torr absolute pressure, and then the chamber, condenser and piping are isolated from the vacuum system. Thereafter, the upper shelf is raised until the cap is no longer sealed but rests loosely on the container. Because of the pressure differential between the evacuated chamber and the containers, the sterilant then vaporizes upon exposure to the deeply evacuated environment and the vapor escapes into the chamber under the gaps between the cap and its container. The system is maintained under a static deep vacuum for a pre-determined time period (e.g. 30 minutes), hence exposing the interior of the freeze dryer to sterilant vapor and achieving the decontamination. Air is vented into the freeze dryer, raising the pressure to about 50 Torr or greater before the chamber is re-evacuated. Then, the entire process can be repeated a number of times so that the desirable level of decontamination or sterilization is achieved. The aeration begins by admitting air into the freeze dryer, raising the pressure to about 100 Torr or greater following by a re-evacuation to 10 Torr or below. This aeration process is then repeated until the desired level of sterilant residual within the chamber is achieved.

In a second embodiment of the invention, the freeze drier system is comprised of a chamber containing at least 3 shelves (bottom, middle and upper), two of which are vertically movable while maintaining the horizontal position stoppable in any vertical position. Containers selectively filled with liquid sterilant are uniformly positioned on each of the bottom and middle shelves. The middle shelf is first lowered to seal loosely fitting caps on the containers on the bottom shelf Thereafter the top shelf is lowered to seal the containers on the middle shelf. The above mentioned process is then carried out sequentially on each shelf wherein the chamber is evacuated, and the upper shelf is raised in order to break the seal on the liquid filled containers, allowing the sterilant to evaporate in the deeply evacuated environment and distribute within the chamber. After a specified time period of exposure to the sterilant vapor, air is vented into the freeze dryer and the chamber and condenser are re-evacuated in order to initiate the process using the liquid filled container on the bottom shelf.

In another embodiment of the invention, the freeze dryer system is comprised of a chamber containing 3 or more vertically movable shelves which are stoppable in any position while maintaining a horizontal position. Containers selectively filled with liquid sterilant are uniformly positioned on each of the shelves. The shelves are all lowered to seal all of the containers. The above mentioned process is then carried out on each shelf thereby exposing the chamber, condenser and piping to a number of sterilant vapor pulses which is equal to the number of shelves in the chamber.

In another embodiment of the invention, a container apparatus is utilized such that multiple sterilize pulses can be accomplished with a single movable shelf. The container apparatus is comprised of multiple individual containers, each having a compression spring, a sealing device and a stop which is of differing lengths for each container. Additionally, the bottoms of the containers have raised dimples permitting the area on the shelf below the container to be sterilized also. Liquid sterilant is placed in each of the individual containers. In using the method of the current invention is aforementioned above, when the upper shelf is raised to a predetermined first level, for example, ⅜ inch, the seal on the first container is broken in the deeply evacuated environment and evaporation of the liquid sterilant contained therein occurs. After an appropriate time period the sterilization pulse is completed by admitting filtered, air the system is then re-evacuated and the upper shelf is raised to a predetermined second level, for example, an additional ⅜ inch until the seal of the second container is broken. The pulsing sterilization process is then repeated until the upper shelf has moved sufficiently far to break the seals on all of the container apparatii.

BRIEF DESCRIPTION OF THE DRAWINGS

The present invention can best be understood by reference to the drawings, in which.

DETAILED DESCRIPTION OF THE DRAWINGS

FIG. 1

The invention will first be described in reference to FIG. 1, which illustrates components of a system for practicing a preferred embodiment of the invention.

Figure 1:
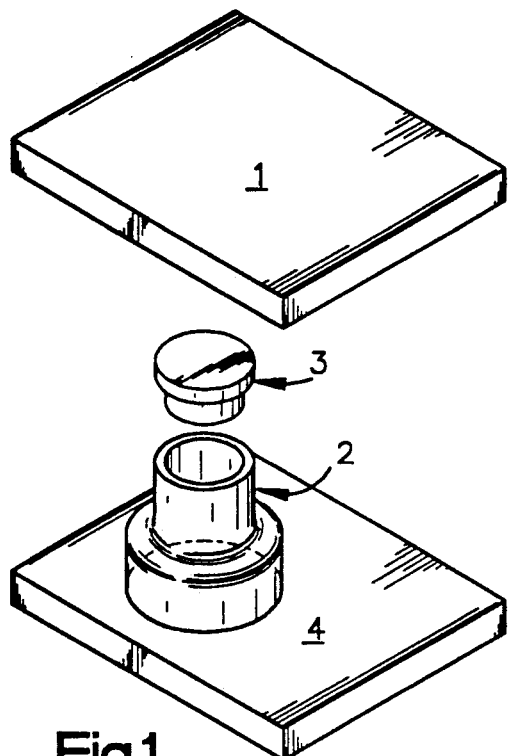
FIG. 1 is a schematic diagram of one embodiment of a system comprising two chamber shelves for use in practicing the method of the present invention.

The system, as depicted in FIG. 1, includes an upper movable shelf 1, container 2, cap 3 which loosely fits onto the container, and lower shelf 4. A predetermined amount of liquid sterilant, preferably hydrogen peroxide or peracetic acid, is poured into container 2. The loose fitting cap 3 is then put in place. The cap is designed so as to avoid horizontal sliding but does not act as a plug to cork the container's opening. The capped container is placed in the center of lower shelf 4. Then the chamber door of the freeze dryer (not shown) is closed and upper shelf 1 is lowered until it presses down on cap 3 and seals shut container 2.

The chamber, condenser and piping are evacuated to below 1 Torr absolute pressure, following which upper shelf 1 is raised until cap 3 is no longer sealed on container 2. The sterilant then vaporizes in the deeply evacuated environment and diffuses out of the container into the freeze dryer. The system remains under a static deep vacuum for a pre-determined time period, exposing the interior of the freeze dryer to hydrogen peroxide vapor.

FIG. 2

Figure 2:
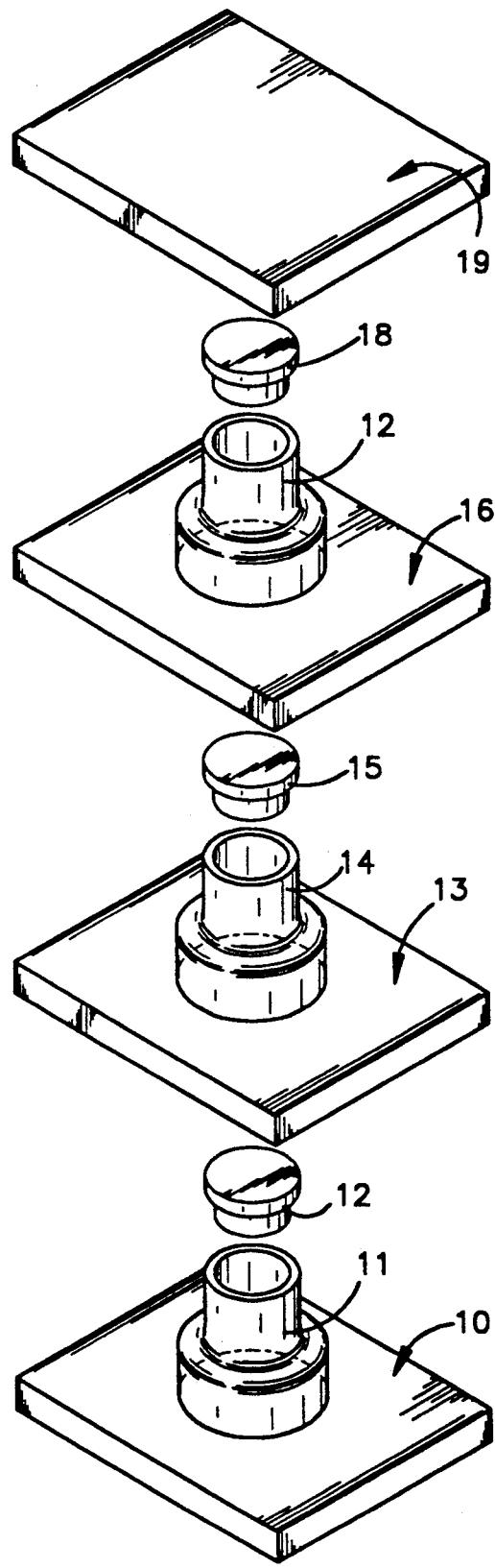
FIG. 2 is a schematic diagram of an alternative system comprising four shelves for use in practicing the method of the present invention.

The system as depicted in FIG. 2 includes top shelf 19, lower shelf 13, and upper shelf 16, all of which are stoppable in any position. Bottom shelf 10, however, remains stationary throughout the decontamination sterilization procedure. Container 11 is first filled with a predetermined amount of liquid hydrogen peroxide and placed in the center of shelf 10. Shelf 13 is lowered, sealing cap 12 on container 11. Container 14 is similarly filled with liquid sterilant, preferably hydrogen peroxide or peracetic acid, and placed in the center of shelf 13. Cap 15 is fitted onto container 14 and shelf 16 is lowered to seal cap 15 onto container 14. Container 17 is then filled with a predetermined amount of liquid sterilant and placed in the center of shelf 16. Cap 18 is loosely fitted onto container 17 and sealed thereon when shelf 19 is lowered, pressing against cap 18 until container 17 is sealed.

The chamber, condenser and piping are evacuated to below 1 Torr absolute. Shelf 19 is then raised until cap 18 no longer seals shut container 17. The sterilant contained in container 17 is thus exposed to the deeply evacuated environment and hence, vaporizes. The system remains under a static deep vacuum for a time period during which the interior of the chamber is exposed to sterilant vapor. Air is then vented into the freeze dryer, raising the pressure to above 50 Torr.

Following aeration, the system is re-evacuated to below 1 Torr. Shelf 16 is then raised until cap 15 no longer seals shut container 14, exposing the sterilant to the deeply evacuated environment and, hence, causing vaporization. The system remains under a static deep vacuum for a specified time period, during which the interior of the chamber is exposed to sterilant vapor. Air is again vented into the freeze dryer, raising the pressure to above 50 Torr.

Finally, shelf 13 is raised in a similar manner and the above described procedure is conducted with respect to container 11.

FIG. 3

Figure 3:
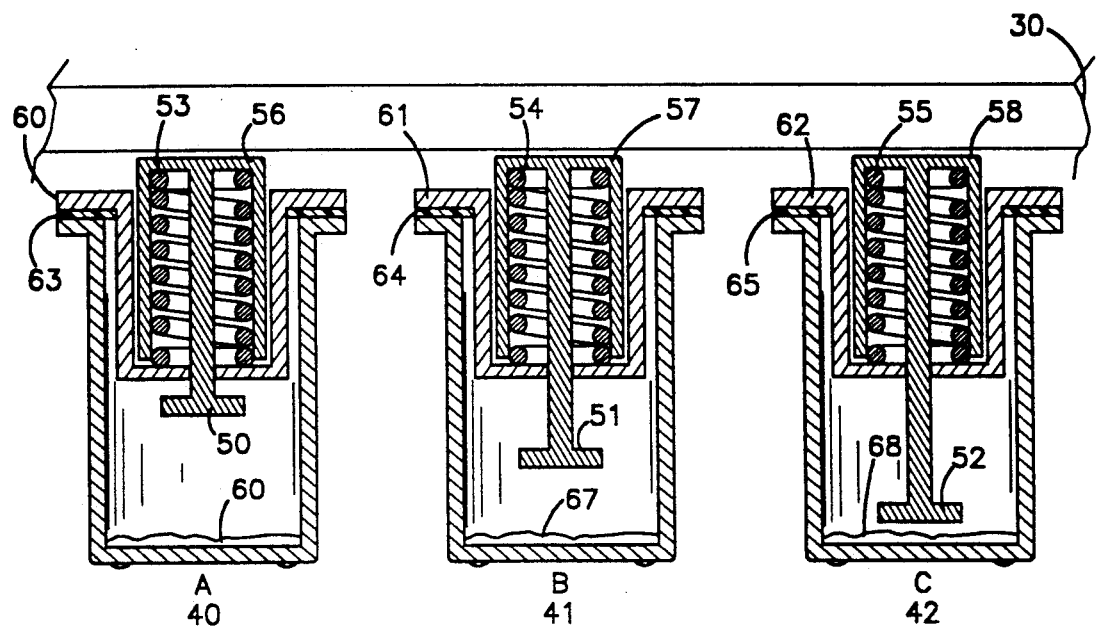
FIG. 3 is a schematic diagram of the container apparatus portion of an alternative system for use in practicing the method of the present invention.

The system as depicted in FIG. 3 includes upper shelf 30, containers 40, 41 and 42, stops 50, 51 and 52, compression springs 53, 54, 55, plungers 56, 57 and 58, caps 60, 61 and 62, and seals 63, 64 and 65. A predetermined amount of liquid hydrogen peroxide is poured into containers 40, 41 and 42 which are sitting on the bottom shelf (not shown).

As the upper shelf 30 is lowered it pushes plungers 56, 57 and 58 down. Compression springs 53, 54 and 55 in turn push caps 60, 61 and 62 which contain seals 63, 64 and 65 against containers 40, 41 and 42 producing a vacuum seal.

The chamber condenser and piping are evacuated to 1 Torr or less. The vacuum piping is closed off. Shelf 30 is raised ¼" past the point when stop 50 prevents compression spring 53 from extending. Cap 60 and seal 63 are no longer compressed against container 40 by the force of compression spring 53. Sterilant 66 is now exposed to the deeply evacuated interior of the chamber so it evaporates and expands to fill the void within the chamber, condenser and piping. After an appropriate time interval, the chamber is vented to 50 Torr (or above) with filtered air.

The chamber, condenser and piping are re-evacuated to Torr or below and the vacuum piping closed off. Shelf 30 is further raised ¼" past the point when stop 51 prevents compression spring 54 from extending. Cap 61 and seal 64 are no longer compressed against container 41 by the force of compression spring 54.

Liquid sterilant solution 67, now exposed to the deeply evacuated state, evaporates and fills the void within the chamber condenser and piping. After an appropriate time interval, the chamber is vented to 50 Torr (or above) with filtered air.

The chamber, condenser and piping are re-evacuated to 1 Torr, or below, and the vacuum piping closed off. Shelf 30 is further raised ¼" past the point when stop 52 prevents compression spring 55 from extending. Cap 62 and seal 65 are no longer compressed against container 42 by the force of compression spring 55.

Liquid sterilant solution 68, now exposed to the deep evacuated environment with the chamber, evaporates and expands to fill the void within the chamber, condenser and piping. After an appropriate time interval, the chamber is vented to 50 Torr (or above) with filtered air.

Evacuations are alternated with filtered air admits until the chamber, condenser and piping are sufficiently aerated to lower the hydrogen peroxide residuals to the desired level.

Figures 4, 5:
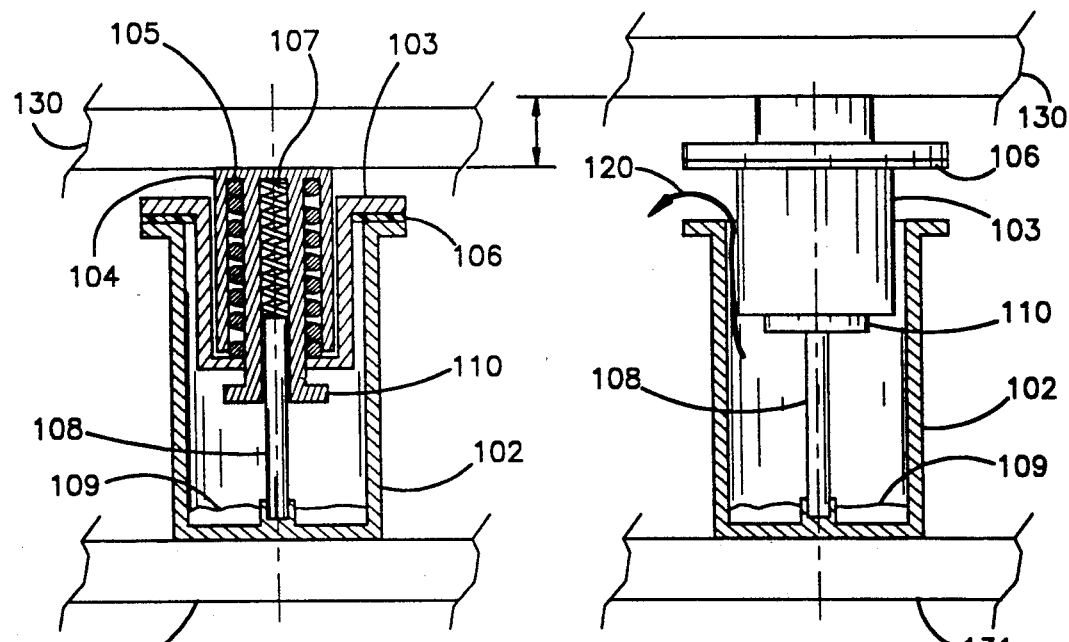
FIGS. 4 and 5 are schematic diagrams of another embodiment of the container apparatus portion of the alternative system for use in practicing the method of the present invention.

FIGS. 4 and 5

An alternate embodiment of the system described in FIG. 3, is depicted in FIGS. 4 and 5 includes upper shelf 130 and lower shelf 131 which compress and seal the container assembly consisting of container 102, plunger 104, cap 103, spring 105, seal 106, spring 107, plunger stop 110, pushrod 108 and sterilant solution 109.

A deep vacuum, typically at or below 1 Torr, is drawn in the freeze dryer chamber (not shown) which contains shelves 130 and 131 as well as the entire container assembly. As shelf 130 begins to move away from shelf 131, compression spring 105 extends until plunger stop 110 rests against the bottom surface of cap 103.

Then, spring 107 pushes plunger 104, cap 103 spring 105, plunger stop 110 and seal 106 against top shelf 130 as it continues to move away from shelf 131. The vacuum within the freeze dryer chamber is sufficiently low so that sterilant solution 109 begins to boil and escapes through annular path 120 as shown in FIG. 5.

Various combinations of the embodiments are possible. For example, a chamber with two movable shelves could utilize three different container apparatii on each shelf. A six pulse sterilization cycle could be produced with only two movable shelves in this manner.

The invention could be used in chambers other than freeze dryers that have movable shelves and are capable of being evacuated. Also, the order in which the shelves move can vary. The top shelf could be stationary and the lower shelves could move.

While the invention is susceptible to various modifications and alternative forms, the preferred embodiments have been described herein in detail. It is to be understood, however, that it is not intended to limit the invention to the specific forms disclosed. On the contrary, it is intended to cover all modifications and alternative forms falling within the spirit and scope of the invention.

What is claimed is:

1. A method for decontaminating a chamber system to a predetermined level, that comprises that steps of:
   a) providing a chamber system having at least a lower and an upper half, at least one of which is vertically movable while maintaining its horizontal position, a condenser, and piping that are fluidly connected to each other and to a vacuum system;
   b) placing at least one container containing a predetermined amount of liquid sterilant into the chamber on at least one shelf;
   c) placing a loose fitting cap on said at least one container;
   d) moving one of the shelves until the adjacent shelf presses against the at least one container cap thereby sealing the container;
   e) evacuating the chamber, condenser and piping to a vacuum of below 1 Torr absolute pressure, wherein the chamber system is isolated from the vacuum system;
   f) moving another of said movable shelves until the cap on the at least one container is no longer sealed on the container;
   g) vaporizing at least a portion of said liquid sterilant by exposing said liquid sterilant to the evacuated chamber environment; and
   h) maintaining the vacuum and exposing the interior of said chamber to sterilant vapor for a pre-determined time until a predetermined level of decontamination is achieved.

2. The method of claim 1, wherein the liquid sterilant in said container is selected from the group consisting essentially of hydrogen peroxide and peracetic acid and mixtures thereof.

3. The method of claim 1, wherein the liquid sterilant in said container is from between about 30% to about 35% by weight concentration of aqueous hydrogen peroxide solution.

4. The method of claim 1, wherein the mass of liquid sterilant is small compared to the mass of the container to prevent freezing.

5. The method of claim 1, wherein the predetermined level of decontamination is sterilization.

6. The method of claim 1, wherein the chamber system is a freeze dryer system.

7. The method of claim 1, wherein the method further comprises repeating steps d) through h) for each additional shelf until a predetermined level of decontamination is achieved.

8. A method for decontaminating a chamber system that comprises the steps of:
   a) providing a chamber system having a bottom, at least one middle and a top shelf, wherein at least two of the shelves are vertically movable while maintaining a horizontal position and which can be stopped in any position, a condenser, and piping that are fluidly connected to each other and to a vacuum system;
   b) placing multiple containers containing a predetermined amount of liquid sterilant into the chamber on at least two of the shelves each of which is directly below and adjacent to one of the other shelves;
   c) placing a loose fitting cap on each container;
   d) selectively moving each movable shelf to press the caps and seal the containers on an adjacent shelf;
   e) evacuating the chamber, condenser and piping to a vacuum below 1 Torr absolute pressure, wherein the chamber system is isolated from the vacuum system;
   f) moving at least one of the movable shelves until the cap on each container on a respective adjacent shelf is released and the container is no longer sealed;
   g) vaporizing the liquid sterilant in each non-sealed container by exposing the liquid to the evacuated chamber;
   h) maintaining the vacuum and exposing the interior of the chamber to sterilant vapor for a first pre-determined time;
   i) venting air into the chamber, thereby raising the pressure within the chamber to about at least 50 Torr;
   j) evacuating the chamber, condenser and piping to a vacuum of below 1 Torr absolute pressure, wherein the chamber system is isolated from the vacuum system;
   k) moving at least a second one of the movable shelves until the cap on each container on a respective adjacent shelf is released and the container is no longer sealed;
   l) vaporizing the liquid sterilant in each non-sealed container by exposing the liquid to the evacuated chamber environment; and
   m) maintaining the vacuum and exposing the interior of said chamber to sterilant vapor for a second pre-determined time until a predetermined level of decontamination is achieved.

9. The method of claim 8, wherein the liquid sterilant is selected from the group consisting essentially of hydrogen peroxide and peracetic acid and mixtures thereof.

10. The method of claim 8, wherein the liquid sterilant is from between about 30% to about 35% by weight concentration of aqueous hydrogen peroxide solution.

11. The method of claim 8, wherein the predetermined amount of liquid hydrogen peroxide is distributed among the containers placed on the chamber shelves.

12. The method of claim 8, wherein the predetermined level of decontamination is sterilization.

13. The method of claim 8, wherein the chamber system is a freeze dryer system.

14. A method for decontaminating a chamber system, which comprises the steps of:
   a) providing a chamber system having a plurality of shelves, at least one of which is vertically movable while maintaining its horizontal position, a condenser, and piping that are fluid connected to each other and to a vacuum system;
   b) placing n sets of containers, each set consisting of at least one container, into the chamber on at least one of the shelves, each container containing a pre-determined amount of liquid sterilant, and wherein each container further comprises a cap assembly, a compressure spring, a plunger, a sealing device, and a bottom assembly such that each set has a cap assembly of a different length;
   c) placing the cap assembly loosely on each container;
   d) moving the movable shelves until the cap assembly on each container is pressed by one of the respective adjacent shelves and seals substantially all of the containers;
   e) evacuating the chamber, condenser and piping to a vacuum of below 1 Torr absolute pressure, wherein the chamber system is isolated from the vacuum system;
   f) moving at least one of the movable shelves to a first predetermined level until the cap assembly is released and the seal on at least one set of the containers is broken;
   g) vaporizing the liquid sterilant by exposing said liquid to the evacuated chamber environment;
   h) maintaining the vacuum and exposing the interior of the chamber to sterilant vapor for a first pre-determined time;
   i) injecting air into the chamber;
   j) re-evacuating the chamber, condenser and piping;
   k) moving at least another movable shelf to another predetermined level until the cap assembly is released and the seal of at least one additional set of containers is broken;
   l) vaporizing the liquid sterilant by exposing said liquid to the evacuated chamber environment;
   m) maintaining the vacuum and exposing the interior of said chamber system to sterilant vapor for another pre-determined time; and
   n) maintaining the vacuum and exposing the interior of the chamber system to sterilant vapor until a predetermined level of decontamination is achieve.

15. The method of claim 14, wherein the bottom assembly of said containers has raised dimples permitting the area on the shelf below the containers to be sterilized.

16. The method of claim 14, wherein the liquid sterilant is selected from the group consisting of hydrogen peroxide and peracetic acid and mixtures thereof.

17. The method of claim 14, wherein the liquid hydrogen peroxide is from between about 30% to about 35% by weight concentration of aqueous hydrogen peroxide solution.

18. The method of claim 14, wherein the predetermined level of decontamination is sterilization.

19. The method of claim 14, wherein the chamber system is a freeze dryer system.

20. The method of claim 14, wherein the liquid sterilant in each container is from about 1 to about 2 grams of liquid hydrogen peroxide.

21. The method of claim 14, wherein the number of sets of containers, n, is any number between 2 and 20 and in which steps (e) through (g) are repeated once for each set of containers.

22. The method of claim 14, wherein the method further comprising repeating steps k) through m) until a predetermined level of decontamination is achieved.

* * * * *